United States Patent [19]

McKinnie et al.

[11] Patent Number: 5,041,687
[45] Date of Patent: Aug. 20, 1991

[54] BROMINATION PROCESS

[75] Inventors: Bonnie G. McKinnie, Magnolia, Ark.; David R. Brackenridge, Baton Rouge, La.

[73] Assignee: Ethyl Corporation, Richmond, Va.

[21] Appl. No.: 199,197

[22] Filed: May 26, 1988

[51] Int. Cl.$^5$ ............................................. C07C 41/00
[52] U.S. Cl. .................................. 568/592; 568/635; 568/637; 568/645
[58] Field of Search ................ 260/694; 568/592, 635, 568/637, 645, 592, 635, 637, 645

[56] References Cited

U.S. PATENT DOCUMENTS

| Re. 32,606 | 2/1988 | Stepniczka | 568/637 |
|---|---|---|---|
| 3,752,856 | 8/1973 | Magy et al. | 260/312 |
| 3,965,197 | 10/1976 | Stepniczka | 260/623 |
| 4,223,169 | 9/1980 | Barda | 568/645 |
| 4,287,373 | 9/1981 | Garman et al. | 568/639 |
| 4,717,776 | 1/1988 | Brackenridge et al. | 568/637 |
| 4,740,629 | 4/1988 | Brackenridge et al. | 568/639 |

FOREIGN PATENT DOCUMENTS 54-44623 4/1975 Japan.

OTHER PUBLICATIONS

*Chemical Abstracts,* Noguchi et al., 90(9):71899a.

*Primary Examiner*—Catherine S. Kilby Scalzo
*Attorney, Agent, or Firm*—Edgar E. Spielman, Jr.

[57] ABSTRACT

This invention relates to the process for preparing partially brominated non-condensed ring polyaromatic product. The process comprises forming a reaction mass by adding a substantially stoichiometric amount of $Br_2$ to a mixture comprising a non-condensed ring polyaromatic, a solvent selected from a group consisting of methylene dibromide, methylene dichloride and mixtures thereof, and a catalyst selected from the group consisting of zirconium halide, iron, ferric chloride and mixtures thereof, the reaction mass being maintained at a temperature within the range of from about 10° to about 50° C. during at least substantially all of the addition; refluxing the reaction mass after the addition is completed or at least nearly completed; and recovering from the reaction mass the partially brominated non-condensed ring polyaromatic product.

14 Claims, No Drawings

BROMINATION PROCESS

BACKGROUND OF THE INVENTION

This invention relates to a process for preparing partially brominated non-condensed ring polyaromatics. Exemplary of such brominated compounds are octabromodiphenyl ether, hexabromodiphenyl ether, pentabromodiphenyl ether, and the like. These partially brominated compounds are useful as flame retardants in various thermoset and thermoplastic formulations.

The processes often used to commercially produce such partially brominated compounds yield a product which is a mixture of polybromo homologs, with the product being identified in accordance with the predominate homolog which is present. For example, a typical octabromodiphenyl ether product would contain hexabromodiphenyl ether, heptabromodiphenyl ether, octabromodiphenyl ether, and nonabromodiphenyl ether, with the octabromodiphenyl ether being the predominant compound, e.g., the octabromodiphenyl ether would comprise at least about 85% of the product. The more specific a process is for the selected homolog, the more desirable the product produced thereby is.

It is therefore an object of this invention to provide a process for preparing a partially brominated non-condensed ring polyaromatic product, which process is highly specific for producing the homolog desired.

THE INVENTION

This invention relates to a process for preparing a partially brominated non-condensed ring polyaromatic product. The process includes: forming a reaction mass by adding a substantially stoichiometric amount of elemental bromine to a mixture which comprises a non-condensed ring polyaromatic, a solvent, and a catalyst, the reaction mass being maintained at a temperature within the range of about 10° to about 50° C. during the period of time needed to at least nearly complete the addition; refluxing the reaction mass after the addition of elemental bromine is completed or nearly completed; and recovering from the reaction mass the partially brominated non-condensed ring polyaromatic product. The solvent can be either methylene dibromide, methylene dichloride or a mixture thereof. The catalyst can be either zirconium halide, iron, ferric chloride or a mixture thereof.

The non-condensed ring polyaromatic reactant can be represented by the formula,

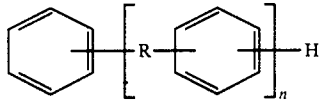

wherein n is a whole integer of at least 1 and may be up to 20 or more, R is an oxygen atom, an alkylene group of up to 6 or more carbon atoms, an oxyalkylene group (—O—R) of up to 6 or more carbon atoms, an oxyalkyleneoxy (—O—R—O—) of up to 6 or more carbon atoms, a sulfur atom, or a carbon-to-carbon single bond. Some examples of these compounds are diphenyl ether, 1,4-diphenoxy benzene, 1,3-diphenoxy benzene, 1,2-diphenoxy benzene, diphenyl methane, 1,2-diphenyl ethane, benzylphenyl ether, 1,2-diphenoxy ethane, diphenyl sulfide, diphenyl, and 1,4-diphenyl butane. Of the non-condensed ring polyaromatic reactants used in this invention, diphenyl ether, diphenyl methane and diphenyl ethane are preferred.

The amount of elemental bromine (Br$_2$) used in the process of this invention is the substantially stoichiometric amount needed to yield the desired predominant homolog in the product. Since one-half of the Br$^-$ provided by the elemental bromine will be substituted to the polyaromatic reactant (the other half being used in the formation of HBr), each substitution site will require one mole of elemental bromine per mole of polyaromatic reactant used. For example, when producing a predominantly decabromodiphenoxy benzene product, the ten substitution sites will require ten moles of elemental bromine per mole of diphenoxy benzene reactant. Further, in producing hexabromodiphenyl ether, the six substitution sites will require substantially six moles of elemental bromine per mole of diphenyl ether reactant. Small amounts of elemental bromine which are in excess of stoichiometric can be used, say 4% of stoichiometric, without unduly affecting the selectivity of the process. The elemental bromine used is preferably substantially free of contaminants which may have an adverse affect on the yield and the composition of the product. This is not to say however, that the elemental bromine must be of such high purity that the economics of the process will be adversely affected.

The solvent used in the process can be methylene dibromide, methylene dichloride or a mixture thereof. The amount of solvent used is that amount which is sufficient to keep the reaction mass in a physical state which is easy to stir or mix. Solvent amounts in excess of this amount are permissible, however, are not needed and would, in most circumstances, merely represent an added cost to the process. In determining the amount of solvent needed the practitioner will have to consider the solubility of the non-condensed ring polyaromatic reactant in the chosen solvent, the stirability of the reaction mass as the process proceeds, and the process equipment available. Thus, the amount of solvent needed is best determined empirically. For example, it has been determined that when the non-condensed ring polyaromatic reactant is diphenyl ether and the solvent is methylene dibromide good stirability with conventional laboratory apparatuses can be achieved with about 3 or more mL of methylene dibromide per gram of diphenyl ether. When the solvent is ethylene dichloride the amount used will be 8 or more mL per gram of diphenyl ether.

A feature of this invention is the use of a zirconium halide, iron or ferric chloride catalyst rather than the conventional aluminum halide catalyst. The use of the aluminum halide catalyst is known for obtainment of perbromination. Any zirconium halide can be used, such as, zirconium chloride, zirconium bromide, zirconium fluoride and mixtures thereof. The most readily available zirconium halide is zirconium tetrachloride. In the reaction mass the catalytic species is very likely zirconium tetrabromide since large amounts of hydrogen bromide are evolved which can convert any of the zirconium tetrahalides to zirconium tetrabromide.

When the catalyst is iron it can most conveniently be supplied to the reaction mass as a powder. If the catalyst chosen is ferric chloride it can be in its conventional catalytic form.

The amount of catalyst used should be an amount which is sufficient to catalyze the partial bromo substitution of the aromatic ring constituents of the non-condensed ring polyaromatic reactant. For zirconium halide the amount used is conveniently within the range of from about 1 to about 5 wt. percent based on the amount of non-condensed ring polyaromatic reactant in the reaction. In the case of iron, an amount within the range of from about 0.5 to about 2 wt. percent on the same basis is useful. For a ferric chloride catalyst, an amount within the range of from about 1 to about 5 wt. percent, on the same basis, can be used in the reaction. A most highly preferred range for zirconium halide is from about 2 to about 3 wt. percent. For iron, a most highly preferred amount is within the range of from about 0.5 to about 1.0 wt. percent and for ferric chloride the amount within the range of from about 2 to about 3 wt. percent is most highly preferred.

A preferred combination of solvent and catalyst is the combination of methylene dichloride and ferric chloride. As can be seen from Example VI particularly good selectivity was achieved in producing a product highly predominant in hexabromodiphenyl ether from the partial bromination of diphenyl ether.

The reaction is conducted by adding elemental bromine to a reaction vessel which contains a mixture of the non-condensed ring polyaromatic, the solvent and the catalyst. During the period in which the addition of the bromine is at least nearly complete, the reaction mass is kept at temperature within the range of from about 10° to about 50° C., preferably 20°-30° C. After the elemental bromine addition is completed or at least nearly completed the reaction mass is brought to its reflux temperature and the process is carried on at that condition for a period from about 2 to about hours to insure that the degree of bromo substitution is achieved. The earliest that the reflux condition should be obtained, is when at least 90% of the elemental bromine addition is completed.

The addition time for the bromine depends upon the scale of the process and upon the ability to control the process temperature and handle evolved hydrogen bromide. On a laboratory scale the addition will require from about 30 to about 60 minutes while on a commercial scale the addition could take from about 2 to about 5 hours or longer.

The process can be run at ambient pressure. Higher or lower pressures may be used but do not offer any significant benefits.

The resultant product can be recovered by any of several conventional methods. A suitable method involves addition of dilute sodium hydroxide solution to the reaction mixture, followed by vigorous agitation to destroy residual bromine. After layer separation, the organic solution is water-washed, dried (azeotropically or by addition of a drying agent) and filtered. The solvent can be vacuum-stripped and the residual solid powdered and air-dried to a constant weight.

The following examples illustrate the process of this invention and the advantages obtained thereby.

Examples I–III are not of this invention and are provided for comparative purposes only.

EXAMPLE I

A 3-necked reaction flask equipped with a reflux condenser, mechanical stirrer and thermocouple dip-leg was connected, in sequence, to a mineral oil bubbler, safety trap and caustic trap. The condenser cold-finger was cooled to 5° C. using a glycol-water circulating pump. The reactor was charged with diphenyl ether (37.7 g, 0.222M) and zirconium tetrachloride catalyst (1.4 g, 0.006M).

Elemental bromine (232.5 g, 1.455M, 9% excess) was charged to a 125 mL, pressure-equalized addition funnel equipped with a 2 MM, metered, teflon stopcock. The elemental bromine was then added to vigorously stirred reaction mass over 1.0 hours while gradually increasing the temperature from 32°-62° C. The reactor temperature was gradually increased to 105° C. over 2.2 hours, while using capillary gas chromatography to monitor product composition.

Water (100 mL) was added and the excess elemental bromine was distilled while product solids formed. Residual elemental bromine and hydrogen bromide was destroyed by addition of 25% sodium hydroxide solution (10 mL). Chlorobenzene (150 mL) was added and the mixture was heated to 90° C. to dissolve the product solids. A 5% solution of sodium sulfite (10 mL) was then added to decolorize the organic layer. The aqueous layer was separated and the organic layer was washed twice with hot water (100 mL). The chlorobenzene solvent was stripped under vacuum (80° C./1 MM) for 18 hours to give a hexabromodiphenyl ether product (134.3 g, 94.0% yield) with melting range 88°-142° C. Product homolog distribution is given in Table 1.

EXAMPLE II

The procedure used in Example I was followed, except that both zirconium tetrachloride (1.1 g, 0.005M) and iron powder (0.06 g, 0.001M) were used as co-catalysts. Elemental bromine addition time was also extended to 2.0 hours. Workup in the usual manner gave a solution of brominated diphenyl ether homologs in chlorobenzene. The gas chromatographic analysis is given in Table I.

EXAMPLE III

A 4-liter resin kettle equipped with the usual auxiliary glassware was charged with diphenyl ether (416.5 g, 2.447M) and zirconium chloride catalyst (18.4 g, 2.447M). Elemental bromine (2712.5 g, 16.974M, 15.6% excess) was added over 2.1 hours at 10°-68° C. The mixture wa brought to 100° C. over 1.0 hours and stirred at 100° C. for 2.5 hours, while monitoring the homolog distribution with capillary gas chromatography.

The bromination was stopped when water (150 mL) was added. Chlorobenzene (1400 mL) was then added, followed quickly by saturated sodium sulfite solution (750 mL). The organic phase was separated, then washed three times with water (1000 mL). The solvent was vacuum-flashed, leaving a residual oil which solidified to give a tacky glass. The glass was reduced to coarse chunks and dried at 75° C./0.5 MM for 16 hours. The resulting solid was then ground to a powder and redried at 80° C./1 MM for 8 hours to give a hexabromodiphenyl ether product (1470.7 g, 97.4% yield) with a melting range 120°-145° C. Product homolog distribution is given in Table I.

Examples 4–6 are of this invention and exhibit the principles thereof.

EXAMPLE IV

A reaction flask equipped as in Example A was charged with diphenyl ether (17.0 g, 0.100M), C.P. methylene dibromide (50 mL) and zirconium chloride catalyst (0.50 g, 0.002M). Elemental bromine (96.0 g, 0.601M) was added to the vigorously stirred mixture over 2.4 hours at 20°–30° C. and the mixture heated over 2.5 hours to 95° C. At this point, hydrogen bromide evolution was negligible and reaction was judged to be complete.

A solution of 50% sodium hydroxide (5.5 g), made up to 40 mLs in water, was stirred into the reaction mixture to give a yellow-colored organic layer. Addition of water (40 mL), followed by vigorous agitation did not change the color. The organic layer was heated to 80° C., transferred to a separator funnel (50 mL methylene dibromide rinse) and washed twice with hot water (100 mL). After drying with magnesium sulfate, the mixture was filtered and the solvent vacuum-stripped to give a hexabromodiphenyl ether product (61.3 g, 95.2% yield). Product homolog distribution is given in Table I.

EXAMPLE V

The procedure used in Example IV was followed except that diphenyl ether (12.0 g, 0.075M), methylene dibromide (50 mL) and iron powder (0.12 g) were reacted with elemental bromine (74.4 g, 0.466M) at 20°–100° C. over ca 4 hours. Partial workup gave a solution of hexabromodiphenyl ether product in methylene dibromide. Product homolog distribution is given in Table I.

EXAMPLE VI

The procedure used in Example IV was followed except that diphenyl ether (11.35 g, 0.068M) in methylene dichloride (100 mL) and ferric chloride (0.3 g) were charged to the reactor. Elemental bromine (66.7 g, 0.417M) was added over 1.0 hours at 20°–30° C. After 3.0 hours reflux, partial workup gave a solution of hexabromodiphenyl ether in methylene dichloride. Product homolog distribution is given in Table I.

TABLE I

| Example No. | Hexabromodiphenyl Ether Product Distribution Area% | | | |
|---|---|---|---|---|
| | $Br_5$ | $Br_6$ | $Br_7$ | $Br_8$ |
| I | 11.4 | 78.8 | 9.3 | 0.40 |
| II | 10.8 | 77.6 | 11.0 | 0.55 |
| III | 7.9 | 80.5 | 11.0 | 0.57 |
| IV | 6.9 | 88.2 | 4.7 | 0.08 |
| V | 6.6 | 87.1 | 5.9 | 0.11 |
| VI | 5.8 | 90.2 | 3.9 | 0.07 |

As can be seen, the processes of Examples I–III, which do not use a solvent and which use a 9 to 15% excess of elemental bromine, do not give the selectivity for the desired hexabromodiphenyl ether homolog as do the processes of this invention which are exemplified by Examples IV–VI. Example VI, which uses a methylene dichloride solvent and a ferric chloride catalyst, gives a specificity for hexabromodiphenyl ether which is exemplary.

What is claimed:

1. A process for partially brominating a non-condensed ring polyaromatic compound of the formula,

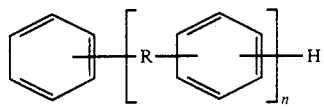

wherein n=1 to about 20 and R is an oxygen atom, an alkylene group having up to about 6 carbon atoms, a sulfur atom or a carbon-to-carbon single bond; said process comprising:
  a. forming a reaction mass by adding a substantially stoichiometric amount of $Br_2$ to a mixture comprising said non-condensed ring polyaromatic compound, a solvent selected from the group consisting of methylene dibromide, methylene dichloride, and mixtures thereof, and a catalyst selected from the group consisting of zirconium halide, iron, ferric chloride and mixtures thereof, said reaction mass being maintained at a temperature within the range of from about 10° to about 50° C. at least during the time period in which said addition of said $Br_2$ is nearly completed;
  b. refluxing said reaction mass after said addition is completed or at least nearly completed; and
  c. recovering from said reaction mass a partially brominated non-condensed ring polyaromatic product.

2. The process of claim 1 wherein said non-condensed ring polyaromatic compound is diphenyl ether.

3. The process of claim 2 wherein said partially brominated non-condensed ring polyaromatic product is predominantly hexabromodiphenyl ether.

4. The process of claim 1 wherein said catalyst is zirconium tetrachloride.

5. The process of claim 1 wherein said catalyst is iron.

6. The process of claim 1 wherein said catalyst is ferric chloride.

7. The process of claim 1 wherein said solvent is methylene dibromide.

8. The process of claim 1 wherein said solvent is methylene dichloride.

9. The process of claim 1 wherein said catalyst is zirconium chloride or iron and said solvent is methylene dibromide.

10. The process of claim 1 wherein said catalyst is ferric chloride and said solvent is methylene dichloride.

11. The process of claim 9 wherein said non-condensed ring polyaromatic compound is diphenyl ether.

12. The process of claim 10 wherein said non-condensed ring polyaromatic compound is diphenyl ether.

13. The process of claim 9 wherein said non-condensed ring polyaromatic compound is diphenyl ether and said partially brominated non-condensed ring polyaromatic product is predominantly hexabromodiphenylene ether.

14. The process of claim 10 wherein said non-condensed ring polyaromatic compound is diphenyl ether and said partially brominated non-condensed ring polyaromatic product is predominantly hexabromodiphenyl ether.

* * * * *